United States Patent
Yang

(10) Patent No.: US 6,195,012 B1
(45) Date of Patent: Feb. 27, 2001

(54) DRIP ANNUNCIATOR

(76) Inventor: Der Chuan Yang, No.21, Alley 9, Lane 27, Sec. 5, Min Sheng E. Rd., Taipei (TW)

( * ) Notice: Subject to any disclaimer, the term of this patent is extended or adjusted under 35 U.S.C. 154(b) by 0 days.

(21) Appl. No.: 09/493,806

(22) Filed: Jan. 28, 2000

(51) Int. Cl.⁷ .................................................. G08B 21/00
(52) U.S. Cl. .................... 340/618; 340/551; 340/623; 340/624; 200/84 C; 604/65; 604/247; 604/254; 604/255
(58) Field of Search .................................. 340/618, 623, 340/614, 624, 551; 604/254, 255, 48, 253, 252, 65, 247, 246, 251; 200/84 C

(56) References Cited

U.S. PATENT DOCUMENTS

| | | | |
|---|---|---|---|
| 4,378,014 | * | 3/1983 | Elkow ................................ 340/551 |
| 4,507,112 | * | 3/1985 | Hillel et al. ......................... 604/65 |
| 4,926,015 | * | 5/1990 | Takahashi et al. ................. 200/84 C |
| 4,970,498 | * | 11/1990 | Hwang .............................. 340/624 |
| 5,527,295 | * | 6/1996 | Wing ................................. 604/254 |

* cited by examiner

Primary Examiner—Edward Lefkowitz
Assistant Examiner—Davetta W. Goins
(74) Attorney, Agent, or Firm—Rosenberg, Klein & Lee

(57) ABSTRACT

A drip annunciator comprises a main body and a needle bottle capable of inserting into a drip bottle for outputting liquid. A buoyancy body is received in the needle bottle, which may move with the liquid level. The bottom of the buoyancy body is installed with a magnet and a magnetic sensor on a control rod at the lower side thereof. Thus, as the liquid level within the drip bottle has descended to a predetermined position, the magnet will actuate the magnetic sensor to be electrically conducted, and then the buzzer at another side emits an alarm or lights up an alarm light so inform one to update the liquid therewithin. Meanwhile, a rolling ball will seal the liquid opening to prevent air to flow inwards so as to safeguard the life of a patient. Besides, another soft tube can be disposed between the liquid transferring tube and the needle bottle, and an adjusting wheel and a screw rod screwedly through the central screw hole and having a tightening block are installed aside. When the adjusting wheel is rotated so that the tightening block to press the soft tube at different level, the output of the liquid is controlled.

11 Claims, 8 Drawing Sheets

DRIP ANNUNCIATOR

FIELD OF THE INVENTION

The present invention relates to an drip annunciator, and especially to a annunciator installed between a drip bottle and a liquid transferring tube, the flow can be adjusted, as the nutrient solution in the drip bottle will be used up, it can be detected so as to emit an alarm or a light to inform the medical members to update the liquid therewithin. Thus, the drip bottle can be used with a higher safety.

BACKGROUND OF THE INVENTION

As shown in FIG. 1, a use of conventional drip bottle 10 is illustrated. The needle 12 for inserting into a bottle is inserted into the soft plug in a drip bottle 10 for transferring the nutrient solution in the bottle. A regulator 13 for controlling the output flow of the nutrient solution is installed at a proper place on the liquid transferring tube 11 so as to supplement the required nutrient to a patient with a proper amount. However, in the simple structure, once the nutrient solution in the drip bottle 10 is exhausted without being supplemented in time. Then, it is possible that the patient will be hurt. Moreover, once air is possible flow into the blood vessel, the life of the patient will be threatened.

SUMMARY OF THE INVENTION

Accordingly, the primary object of the present invention is to provide a drip annunciator, as the level of the liquid in the drip bottle is too low, an alarm is emitted to inform the guarding people and seal the opening the liquid. In the present invention, the buoyancy principle and magnetic attraction principle are used. A buoyancy body is received in the needle bottle in the needle bottle, and a magnet is installed at the bottom of the buoyancy body. Meanwhile, a magnetic sensor is installed at a proper place thereunder, which serves to be electrically connected to a buzzer, an alarming light or other annunciator so that as the liquid level in the drip bottle descends to a preset level, due to magnetic attraction, the magnetic sensor will actuate to be electrically conductive so that the buzzer emits an alarm voice or the alarming light will light up to inform other medical member or other people to update or supplement new liquid.

Another object of the present invention is to provide a drip annunciator. In the main body of the present invention, the drip annunciator of the present invention can be sealed in force. In the present invention, another movable control rod for bearing a magnetic sensor is installed at the main body so that by controlling the control rod, the magnetic sensor can separate from the magnet at a proper time.

A further object of the present invention is to provide a drip annunciator. As the liquid level is too low, not only an alarm is emitted, but also pipe line is sealed at the same time to prevent air to be input. In the present invention, a buoyancy body is received in the needle bottle and capable of moving with the liquid level, a rolling ball is disposed at one side of the buoyancy body so that as the liquid level descends to a preset level to actuate a buzzer to emit an alarm voice, the rolling ball will seal the liquid outlet to interrupt the supplement of nutrient solution in order to avoid that as nutrient solution exhausts, air will flow into the drip bottle. Therefore, by the present invention, the life and safety of the patient is retained.

An yet object of the present invention is to provides a drip annunciator, wherein a soft tube is further installed between the needle bottle and the liquid transferring tube, and an rotatable adjusting wheel is further installed aside. An screw rod with a tightening block is arranged at the central screw hole of the adjusting wheel. By rotating the adjusting wheel, the tightening block will press the soft tube with different levels so as to control the output of the liquid conveniently.

The various objects and advantages of the present invention will be more readily understood from the following detailed description when read in conjunction with the appended drawing.

DETAILED DESCRIPTION OF THE PREFERRED EMBODIMENTS

Figure 1:
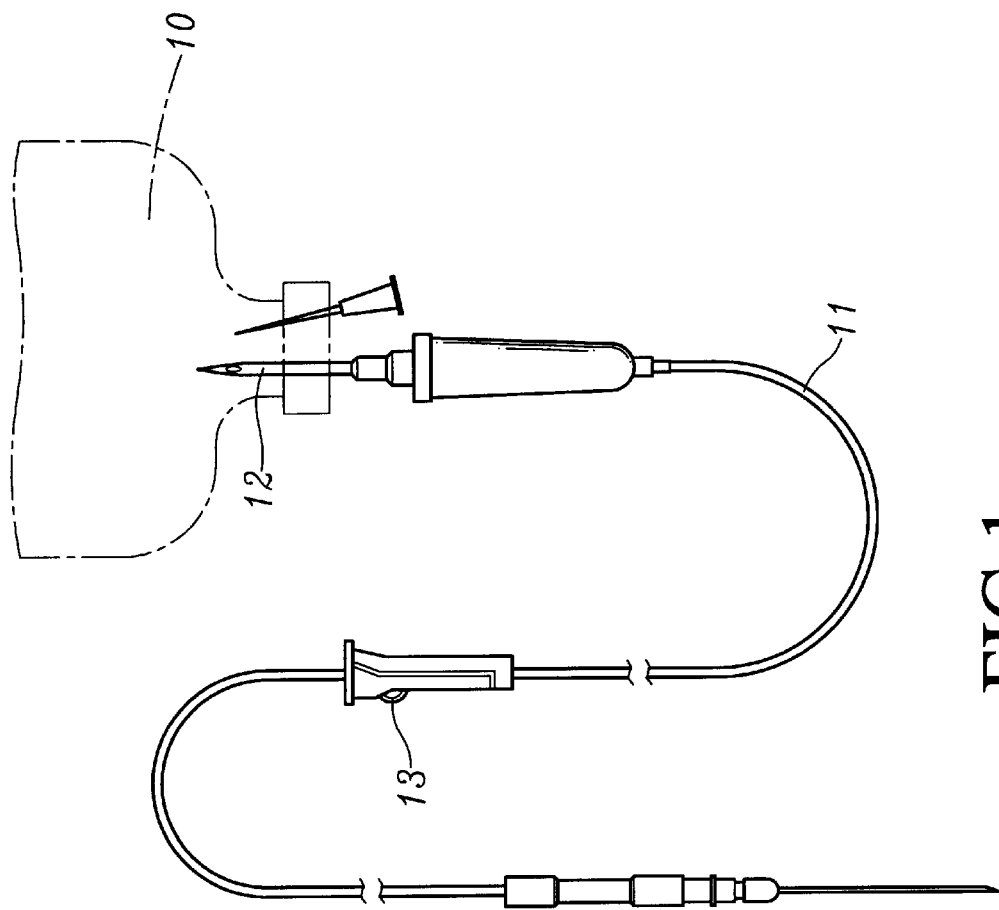
FIG. 1 is a structural schematic view showing the use of a conventional drip bottle.
Figure 2:
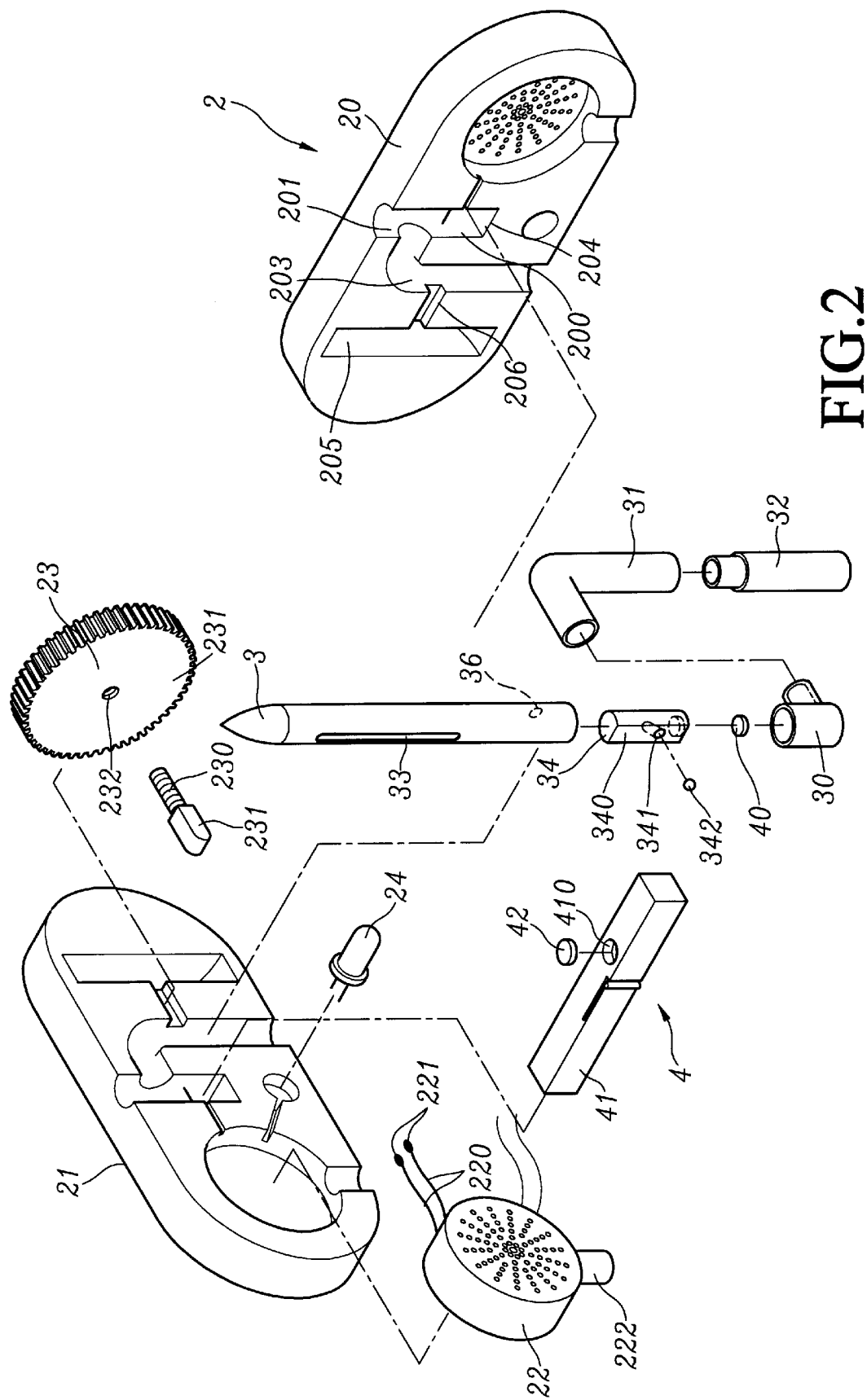
FIG. 2 is an exploded perspective view of the structure according to the present invention.
Figure 3:
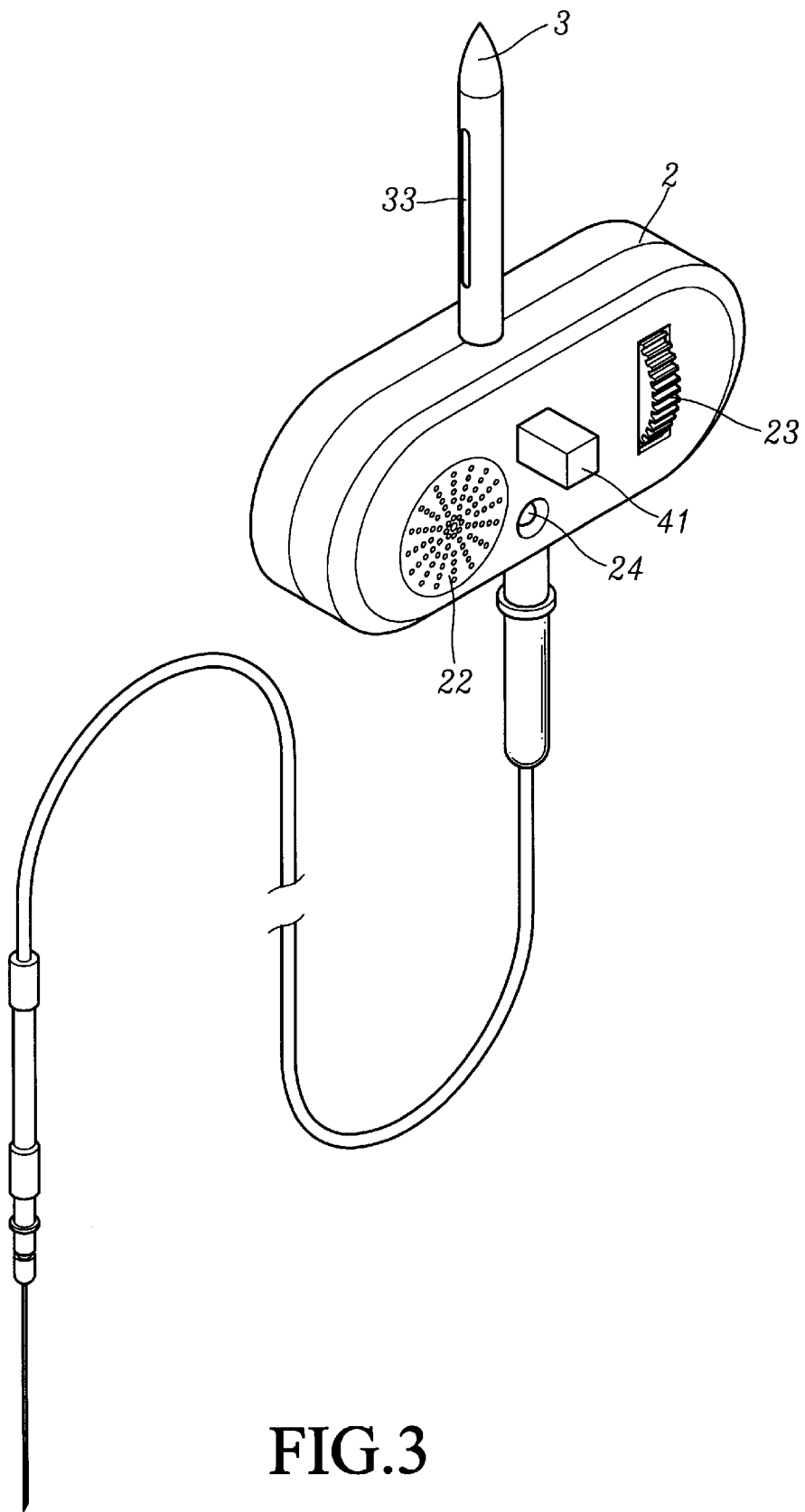
FIG. 3 is an assembled perspective view showing the structure of the present invention.

With reference to FIGS. 2 to 11, the relative figures about one preferred embodiment of the drip annunciator according to the present invention are illustrated. The drip annunciator of the present invention includes a main body 2 formed by a first half case 20 and a second half case 21, a cavity 200 extending upwards and downwards are installed therewithin. A lateral side of the cavity 200 is further installed with an L shape through hole 203 connected to the cavity 200, and an L shape adapting sleeve 30 is installed at the connection therebetween. The bottom of the cavity 200 has a penetrating hole 204 horizontally penetrating therethrough. Besides, a positioning groove 205 is arranged to be parallel to the lateral side of the through hole 203 for being receiving an adjusting wheel 23. At one side of the positioning groove 205 facing to the through hole 203 is formed with a via hole 206 for being screwed through the central screw hole 232 of the adjusting wheel 23. The screw rod 230 of the tightening block 231 can be screwed thereinto and is movable backwards and forwards by rotating the adjusting wheel 23. Moreover, one side of the main body 2 is installed with a buzzer 22 or other annunciator with alarming function. The buzzer is further installed with a receptacle 222.

Figure 4:
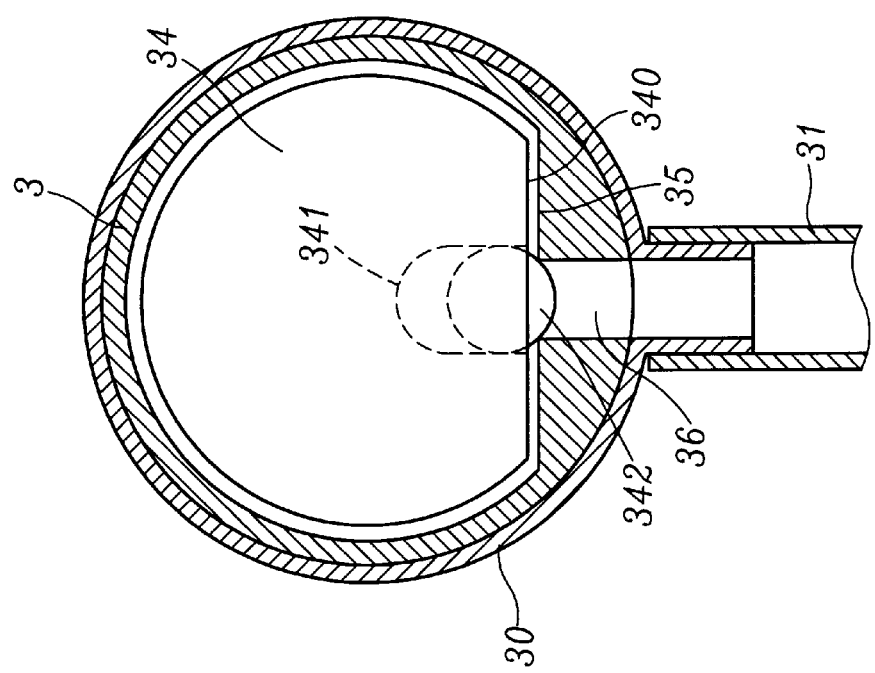
FIG. 4 is a radial schematic cross sectional view showing that the rolling ball at the buoyancy body in the present invention seals the liquid outlet of the needle bottle.

A hollow needle bottle 3 has a bottom for being inserted into one end of the adapting sleeve 30 in order to be inserted into the drip bottle 5. Another end of the adapting sleeve 30 is further connected to a soft tube 32 extending along the through hole 203 for being further connected to a liquid transferring tube 32 at the lower side. The tube wall of the needle bottle 3 is installed with an axial extending liquid inlet 33, while the interior thereof is received with a buoyancy body 34 moving the water surface, as shown in FIG. 4. An axial tangent plane 35 is at the lateral side with respective to the inner wall of the liquid outlet 36 at the bottom thereof. Meanwhile, a tangent plane 340 is installed at the respective lateral side of the buoyancy body 34. The tangent plane 340 is installed with a downward inclined concave hole 341. A rolling ball 342 is received within the concave hole 341. Therefore, as the buoyancy body 34 descends with the liquid surface, by the tangent plane 340 and tangent plane 35, the rotation of the buoyancy body 34 is confined so that as the liquid surface descends to a critical height. The rolling ball 342 exactly rolls down automatically to seal the liquid outlet 36 so as to interrupt the output of the liquid and seal the liquid transferring tube 32.

A magnet 34 is installed at the bottom of the buoyancy body 34 and a magnetic sensor 4 electrically connected to the buzzer 22 is installed at a proper position of the main body 2 of the magnet 40. On embodiment of the magnetic sensor 4 includes two electric joints 221 installed at the bottom of the adapting sleeve 30 and a magnetic guide body 42 installed in the groove 420 on the controlling rod 41 in the penetrating hole 204 and movably lifting, or device which is electrically conductive by a reed switch or other magnetic force.

Figure 5:
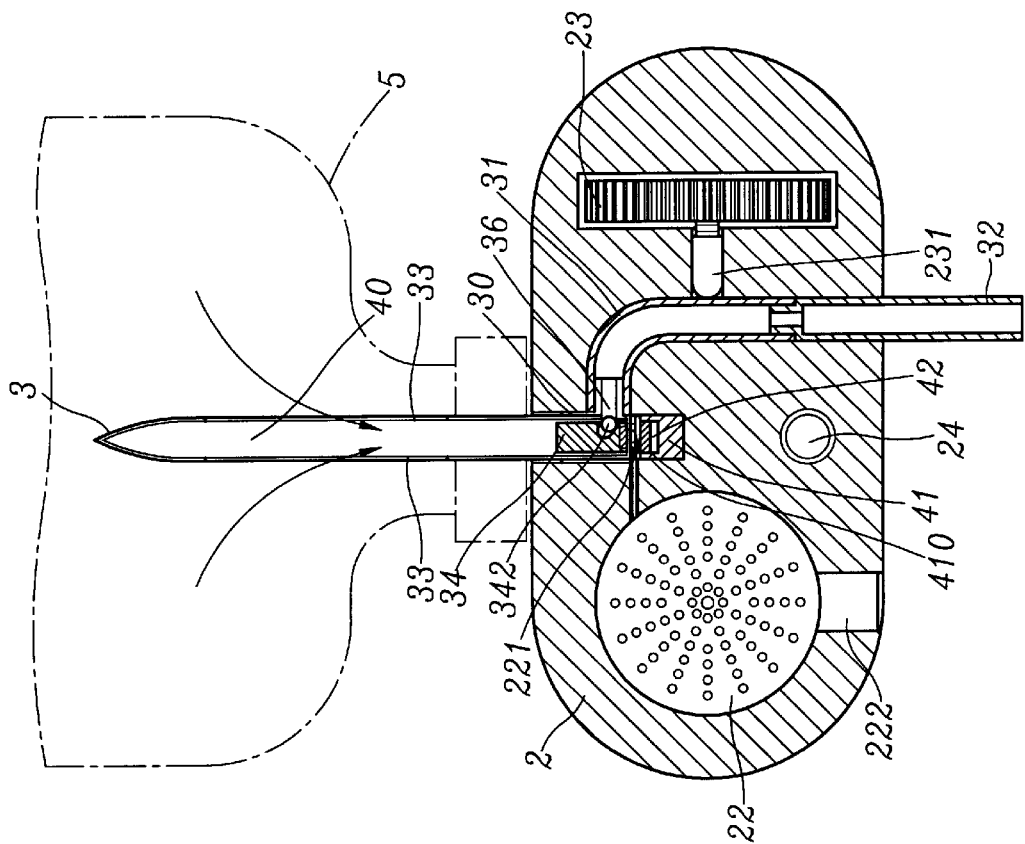
FIG. 5 is a schematic cross sectional view showing a general use of the present invention.
Figure 6:
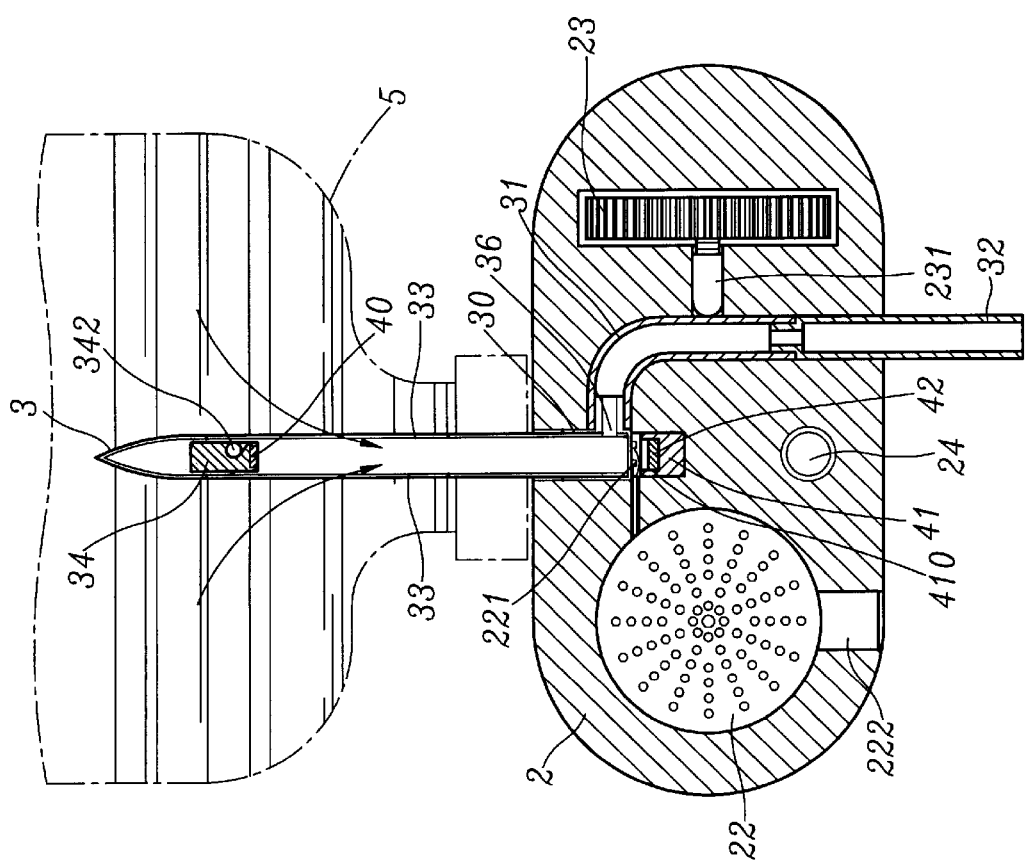
FIG. 6 is a schematic cross sectional view showing that the nutrient solution in the drip bottle of the present invention is almost used up and then a buzzer is actuated to emit an alarm.
Figure 7:
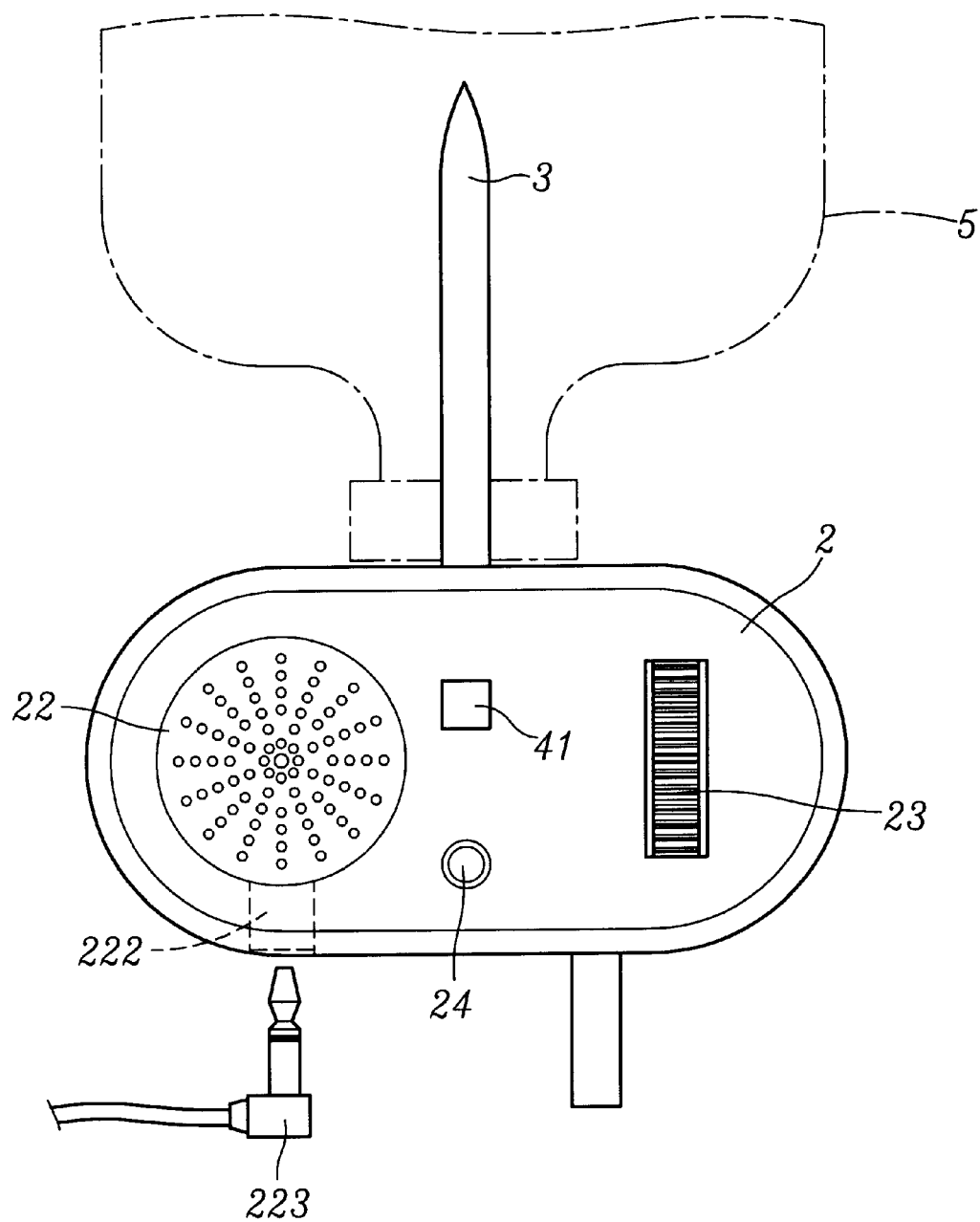
FIG. 7 is a schematic view showing the use of the present invention.
Figure 8:
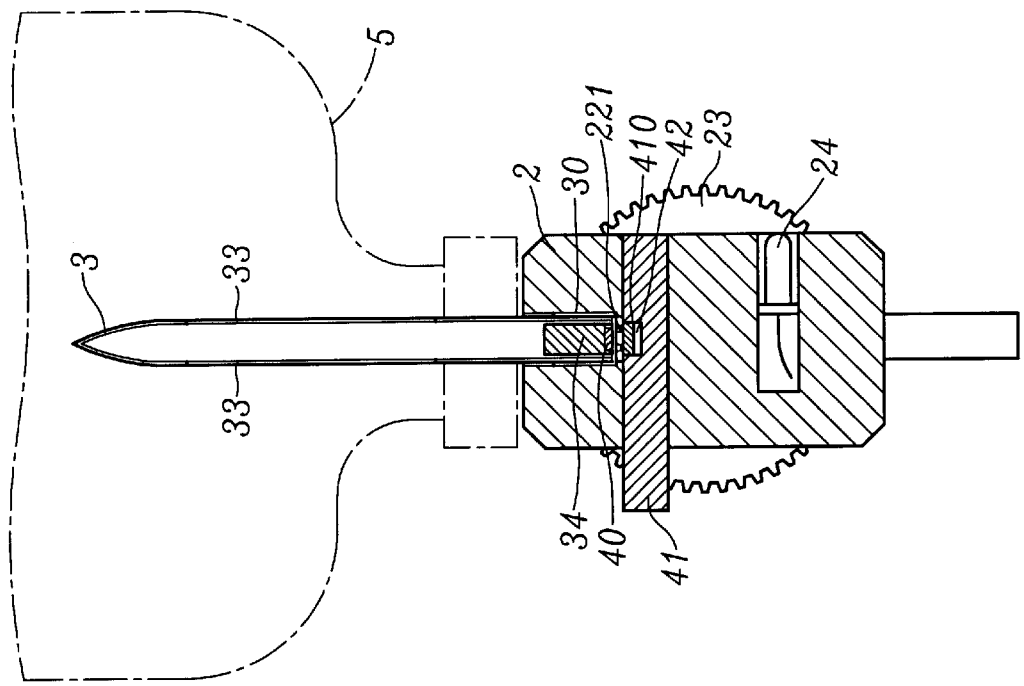
FIG. 8 is a schematic cross sectional view at another orientation showing that the nutrient solution in the drip bottle of the present invention is almost used up and then a buzzer is actuated to emit an alarm.

Thereby, as shown in FIG. 5, in using, the needle bottle 3 is inserted into a drip bottle 5 so that nutrient solution can flow into the needle bottle 3 through the liquid inlet 33. Then, it is output by the soft tube 31 and liquid transferring tube 32 to the body of a patient. While as using the nutrient solution as that liquid level descends to a predetermined critical level, the buoyancy body 34 within the needle bottle 3 will descend with the liquid level to automatically cause the rolling ball 342 to seal the liquid opening 36, as shown in FIG. 6, to prevent air to flow into the bottle so as to harm the patient's body. Alternatively, the magnet 40 at bottom of the buoyancy body 34 will abstract the magnetic guiding body 42 to lift upwards so as to contact the two joints 221 at the bottom of the adapting sleeve 30. Therefore, the two joints 221 are electrically conductive so as to actuate the buzzer 22 to emit a proper alarm and thus to inform the medical members or the guarding people to supplement new liquid in time to steady the sickness of the patient.

However, in sleeping, in order not to interrupt the patient due to the buzz noise, the connecting plug 223 originally to the guardroom of the medical members is connected to a receptacle 222 attached to the buzzer 22 so that the alarm message only transfers to the guardroom, or lights up an alarming light 24 at the main body 2 in order not to interrupt the sleep of the patient.

Figure 9:
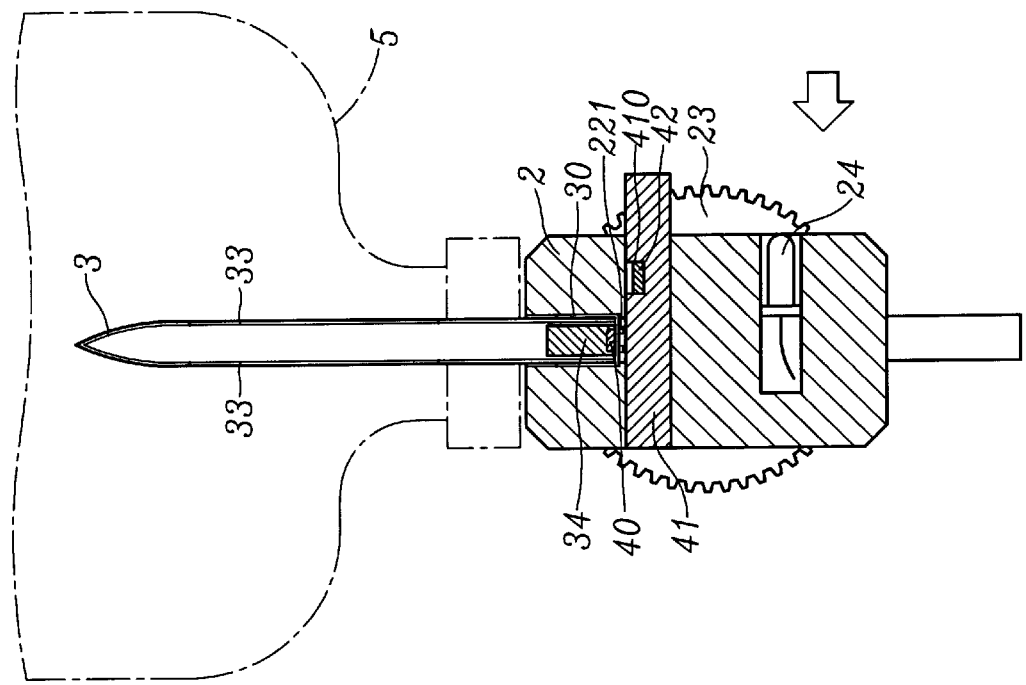
FIG. 9 is a structural schematic cross sectional view showing the buzzer being turning off in force in the present invention.
Figure 10:
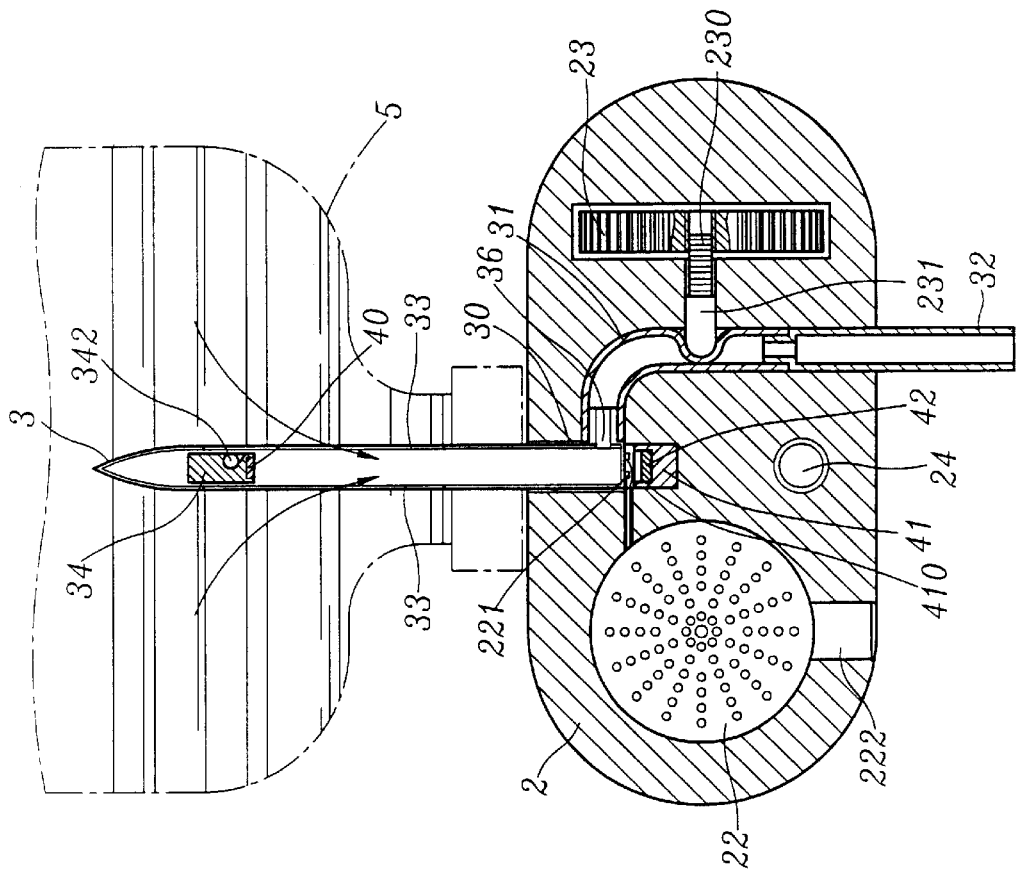
FIG. 10 is a structural schematic cross sectional view showing that in the present invention, the adjusting wheel is rotated to a full open position.

As the use in aforesaid condition with referring to FIG. 6, in order to prevent that two joints 221 are conductive continuously due to the contact of iron pieces 42 or to prevent that since the needle bottle 3 does not be inserted into the drip bottle 5 so that the buoyancy body 34 is still in the bottom of the needle bottle 3 and thus the buzzer 22 emits continuously, as shown in FIG. 9, the control rod 41 can be pushed to cause the magnetic guiding body enforce the iron piece 42 to separate from the two joints 221 and therefore, a manual turning off is formed to shut down the buzzer 22 for preventing interruption.

Figure 11:
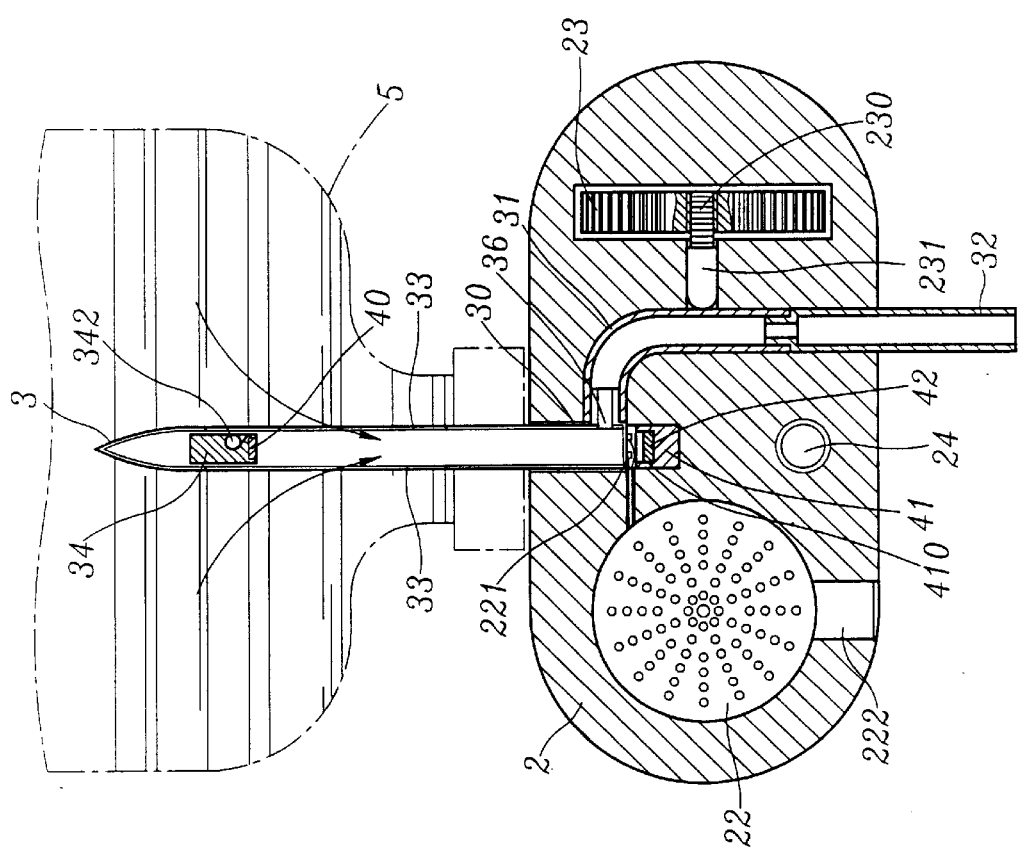
FIG. 11 is a structural schematic cross sectional view showing that in the present invention, the adjusting wheel is rotated to a full close position.

Moreover, in order to match the different timing of different patients, the flow of the liquid transferring tube 32 can be controlled by rotating the adjusting wheel 23. The critical structure is that the adjusting wheel 23 and the screw rod 230 of the tightening block 231 may axially move by rotation. While in whole open, the screw rod 230 and tightening block 231 withdraws from the soft tube 31 to release the tightening pressure so to retain the liquid in full flow. However, as desired, by rotating the adjusting wheel 23, the screw rod 230 and the tightening block 231 will move forward to resist against the soft tube 31, as shown in FIG. 11, by reduction of the radial surface of the tube, the liquid flow can be decreased or even be interrupted. Therefore, the operation is more convenient, easily and comfort to achieve a preferred guarding effect.

Although the present invention has been described with reference to the preferred embodiments, it will be understood that the invention is not limited to the details described thereof. Various substitutions and modifications have been suggested in the foregoing description, and others will occur to those of ordinary skill in the art. Therefore, all such substitutions and modifications are intended to be embraced within the scope of the invention as defined in the appended claims.

What is claimed is:

1. A drip annunciator comprising:

a main body having a cavity extending from the top thereof, a lateral side of the cavity being installed with a through hole communicated with exterior of the main body, an adapting sleeve being installed at the connection of the cavity and the through hole, moreover, an annunciator being arranged at a proper place in the main body;

a needle bottle being inserted into one end of the sleeve at the bottom end thereof so that a top end thereof can be inserted into the drip bottle, a liquid outlet near the bottom thereof exactly facing another end of the adapting sleeve, while the opening of this end can be connected to a liquid transferring tube, and the tube wall of the needle bottle being installed with an axial liquid inlet which is communicated outwards;

a buoyancy body being received within the needle bottle and moving with the liquid level, and a magnet being installed at the bottom thereof; and a magnetic sensor being installed at the main body near the bottom of the needle bottle and being electrically connected to the annunciator, as the magnet is near the magnetic sensor due to the descending of the liquid surface, the annunciator will be conductive due to magnetic induction to actuate the annunciator to emit an alarm message.

2. The drip bottle as claimed in claim 1, wherein the magnetic sensor includes two spaced electric joints installed at the bottom of the adapting sleeve and a magnetic guiding body is installed below the two joints, the magnetic guiding body can be attracted by the magnet to rise up to electrically contact with the two joints simultaneously so as to electrically conduct one magnetic guiding body.

3. The drip bottle as claimed in claim 1, wherein the magnetic sensor is a reed switch.

4. The drip bottle as claimed in claim 1, wherein the annunciator is a buzzer.

5. The drip bottle as claimed in claim 4, wherein an plug in receptacle is further installed at the buzzer for being connected to a connecting plug in a guardroom and other monitoring places so as to stop the buzz of the buzzer temporarily, thus, the alert signal can be transferred to the monitoring place for informing guarding members.

6. The drip bottle as claimed in claim 5, wherein an alarm light is further installed on the main body as the connecting receptacle is connected to the plug in receptacle and emits an alarm, the alarm light will light up.

7. The drip bottle as claimed in claim 1, wherein a control rod movably horizontally is transversally penetrated through the bottom of the cavity, the main body of the magnetic sensor is installed on the control rod, by pushing the control rod, the magnetic sensor move to be near the magnet or separates from the magnet.

8. The drip bottle as claimed in claim 1, wherein a hole is installed at one side of the buoyancy body within the needle bottle, a rolling ball is installed within the hole, as the buoyancy body moves to a proper place with the liquid level, the rolling ball rolls out to seal the liquid outlet communicating to the liquid transferring tube.

9. The drip bottle as claimed in claim 8, wherein an axial formed tangent plane is formed at the inner wall of the needle bottle with respective to one side of the liquid outlet, another, one side of the buoyancy body is installed with a respective tangent plane, so that the buoyancy body can move with the liquid level without rotation so as to retain the orientation of the rolling ball to the liquid outlet.

10. The drip bottle as claimed in claim 1, wherein a soft tube extending along the through hole is installed at one opening at the adapting sleeve.

11. The drip bottle as claimed in claim 10, wherein an adjusting wheel substantially parallel to the soft tube and for adjusting direction is received within the main body, the center screw hole of the adjusting wheel screwedly passes through a screw rod, the front end of the screw rod is disposed with a tightening block so that as the adjusting wheel is rotated, the screw rod and the tightening block are axially moved so as to press the soft tube with different levels for adjusting the flow.

* * * * *